(12) United States Patent
Young et al.

(10) Patent No.: US 9,504,627 B2
(45) Date of Patent: Nov. 29, 2016

(54) MEDICATED MODULE FOR A DRUG DELIVERY DEVICE

(75) Inventors: Alasdair George Young, Oxfordshire (GB); Daniel Thomas De Sausmarez Lintell, Warwickshire (GB); David Richard Mercer, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 341 days.

(21) Appl. No.: 14/112,447

(22) PCT Filed: Apr. 19, 2012

(86) PCT No.: PCT/EP2012/057159
§ 371 (c)(1),
(2), (4) Date: Oct. 17, 2013

(87) PCT Pub. No.: WO2012/143441
PCT Pub. Date: Oct. 26, 2012

(65) Prior Publication Data
US 2014/0039404 A1    Feb. 6, 2014

(30) Foreign Application Priority Data

Apr. 21, 2011  (EP) .................................. 11163400

(51) Int. Cl.
| A61M 5/31 | (2006.01) |
| A61J 1/06 | (2006.01) |
| A61M 5/24 | (2006.01) |
| A61M 5/32 | (2006.01) |
| A61M 5/315 | (2006.01) |
| A61M 5/50 | (2006.01) |
| A61M 5/178 | (2006.01) |

(52) U.S. Cl.
CPC .............. *A61J 1/06* (2013.01); *A61M 5/2422* (2013.01); *A61M 5/2448* (2013.01); *A61M 5/3146* (2013.01); *A61M 5/326* (2013.01); *A61M 5/3294* (2013.01); *A61M 5/2466* (2013.01); *A61M5/31533* (2013.01); *A61M 5/50* (2013.01); *A61M 5/504* (2013.01); *A61M 2005/1787* (2013.01); *A61M 2005/3128* (Continued)

(58) Field of Classification Search
CPC ........... A61M 5/2448; A61M 5/3146; A61M 5/3294; A61J 1/06
See application file for complete search history.

(56) References Cited

U.S. PATENT DOCUMENTS 8,277,421 B2  10/2012  Koyama et al.
8,728,027 B2   5/2014  Jensen et al.
(Continued)

FOREIGN PATENT DOCUMENTS

JP   2001190689 A   7/2001
JP   2005510308 A   4/2005
(Continued)

OTHER PUBLICATIONS

Form PCT/IB/326, Notification Concerning Transmittal of International Preliminary Report on Patentability.
(Continued)

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A medicated module includes (i) a rotatable reservoir body comprising (a) a flow path and (b) a medicament-reservoir profile and (ii) a pin feature disposed in the rotatable reservoir body, the pin feature comprising a medicament-cavity profile. The medicated module also includes a second medicament, wherein the second medicament is held in a reservoir formed at least in part by the medicament-reservoir profile and the medicament-cavity profile, and wherein, prior to dispense, the second medicament is filled to at least the proximal end of the medicament-cavity profile.

12 Claims, 12 Drawing Sheets

(52) U.S. Cl.
CPC ........ (2013.01); *A61M 2005/3247* (2013.01); *A61M 2005/3267* (2013.01); *A61M 2205/583* (2013.01); *A61M 2205/584* (2013.01); *A61M 2205/6045* (2013.01)

(56) References Cited

U.S. PATENT DOCUMENTS

| | | |
|---|---|---|
| 2010/0198151 A1 | 8/2010 | Koyama et al. |
| 2012/0022496 A1* | 1/2012 | Causey ............ A61M 5/14244 604/500 |

FOREIGN PATENT DOCUMENTS

| | | |
|---|---|---|
| WO | 2009013844 A1 | 1/2009 |
| WO | 2010139671 A1 | 12/2010 |
| WO | 2010139672 A1 | 12/2010 |
| WO | 2010139676 A1 | 12/2010 |

OTHER PUBLICATIONS

English Translation of Notification of Reasons for Refusal issued in Japanese Patent Application No. 2014-505725 dated Mar. 22, 2016.

* cited by examiner

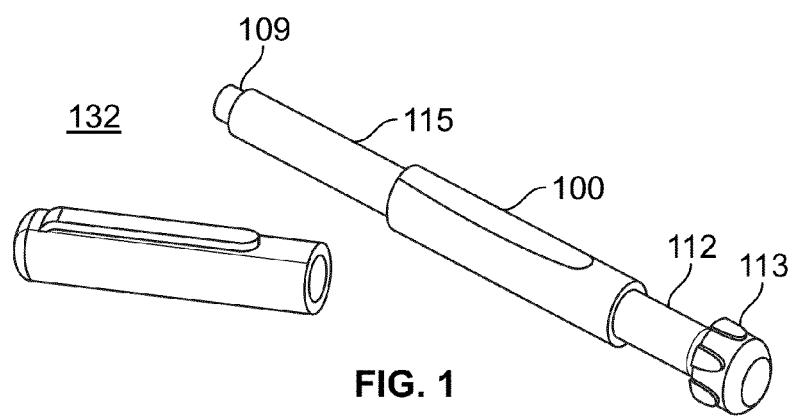
FIG. 1
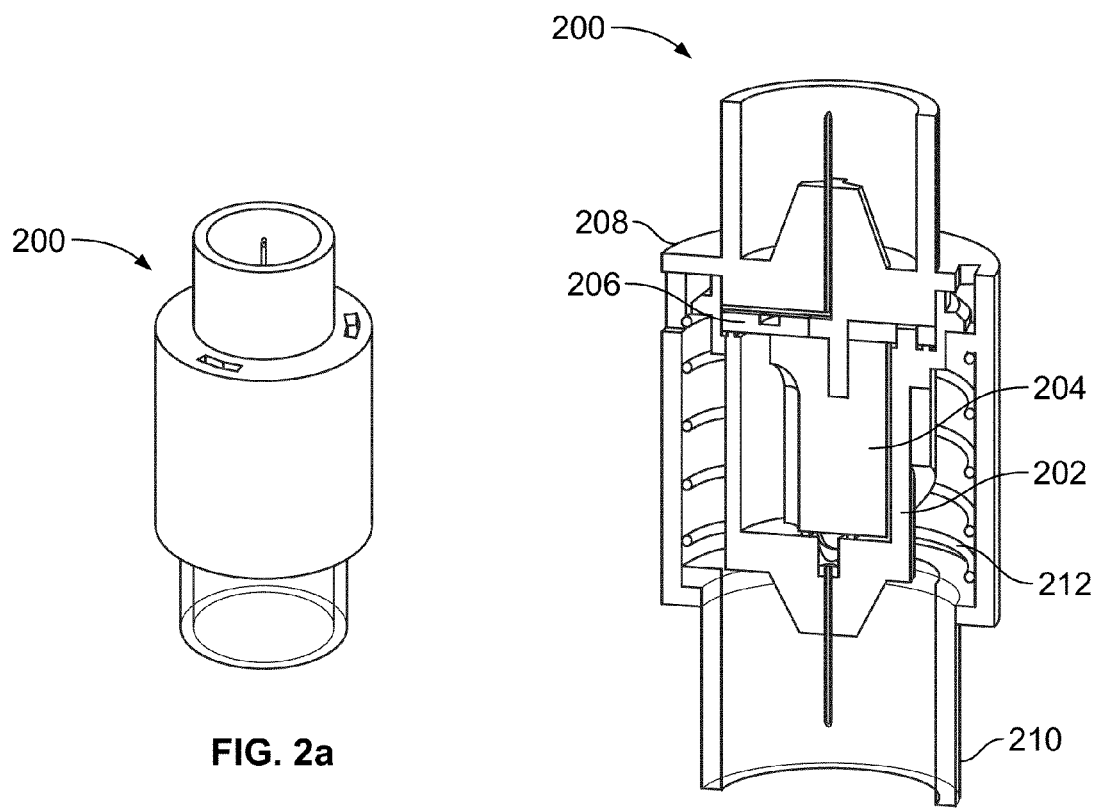
FIG. 2a
FIG. 2b

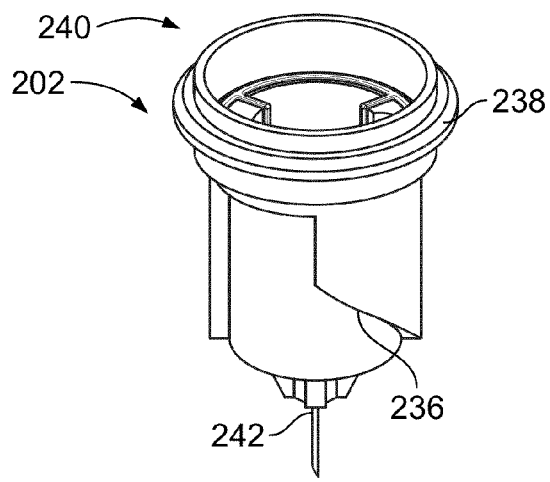
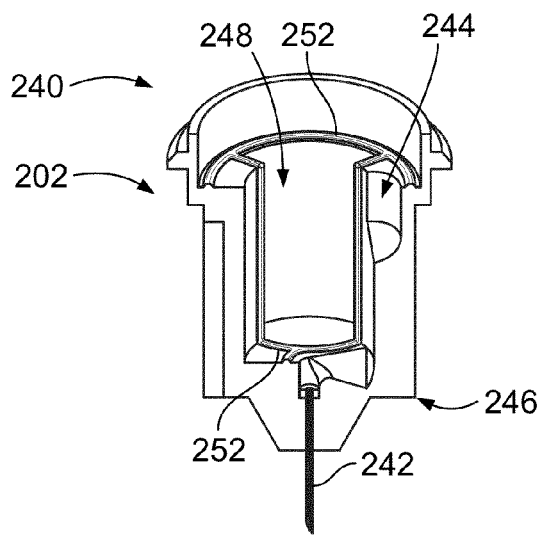
FIG. 6a  FIG. 6b
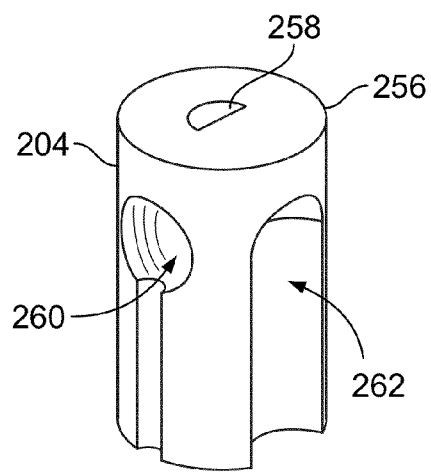
FIG. 7

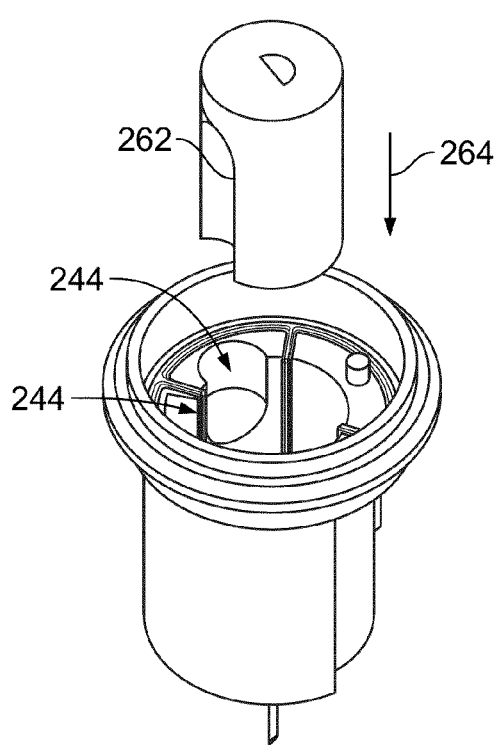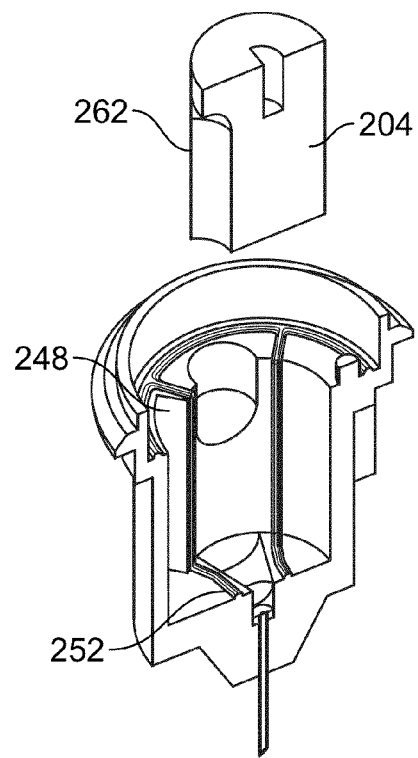
FIG. 8a  FIG. 8b
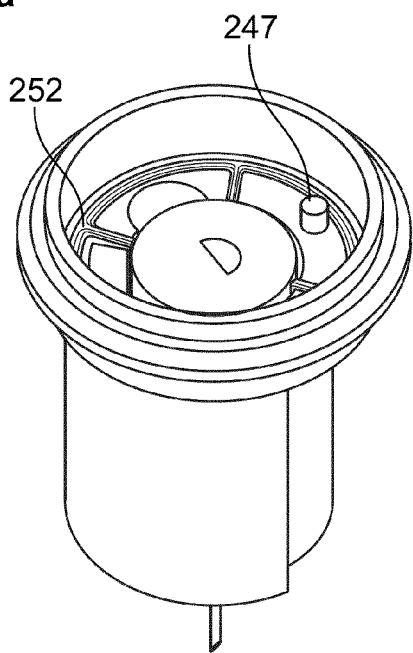
FIG. 9

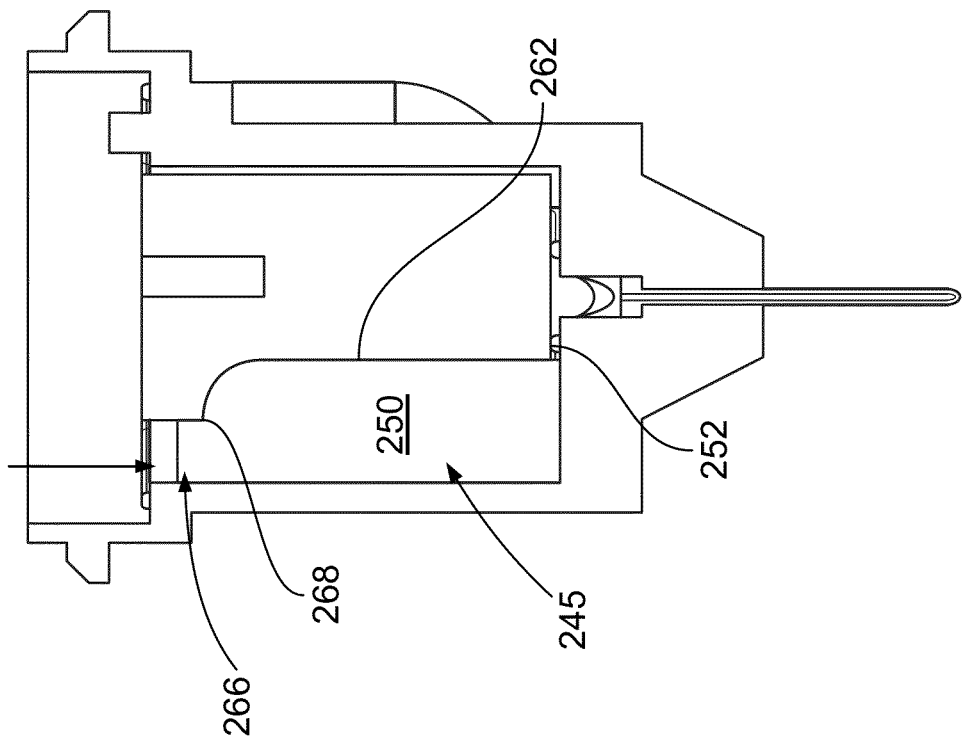
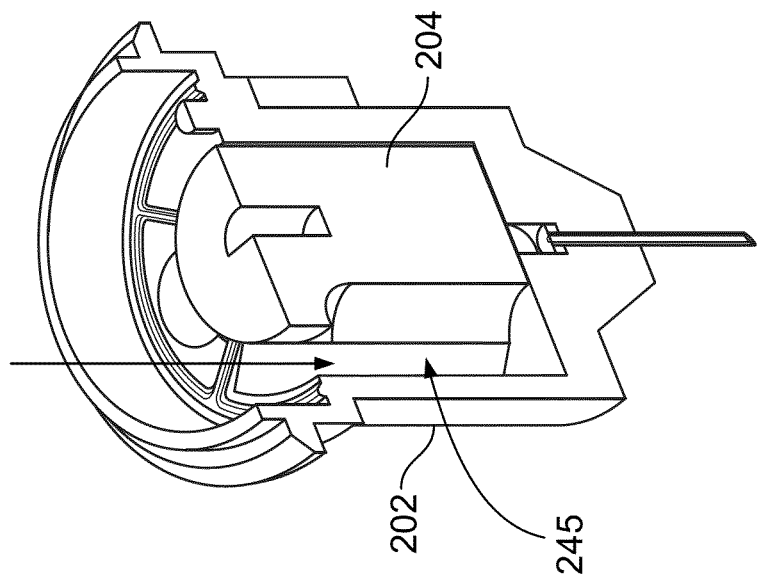
FIG. 10b
FIG. 10a

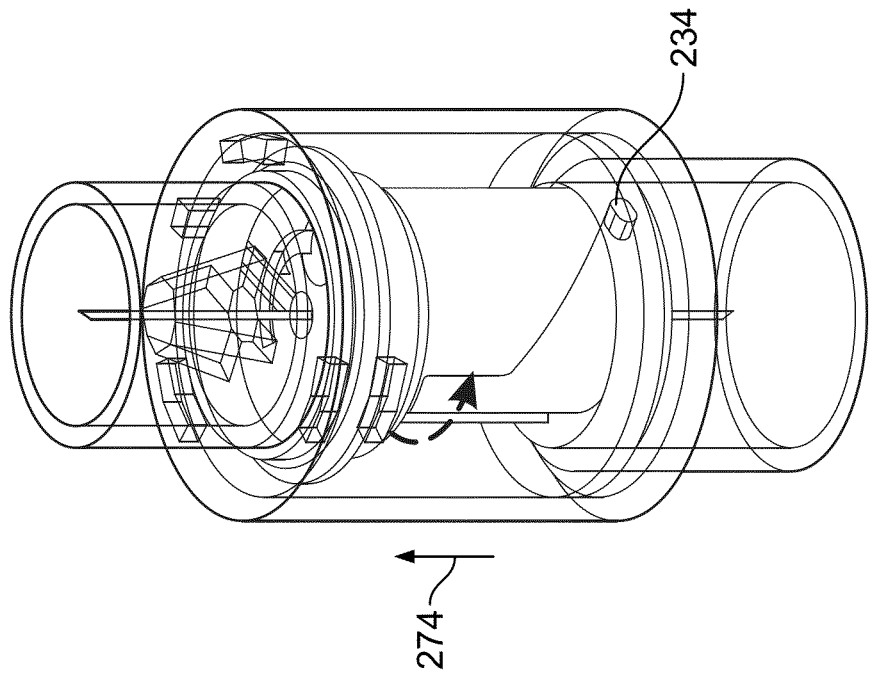
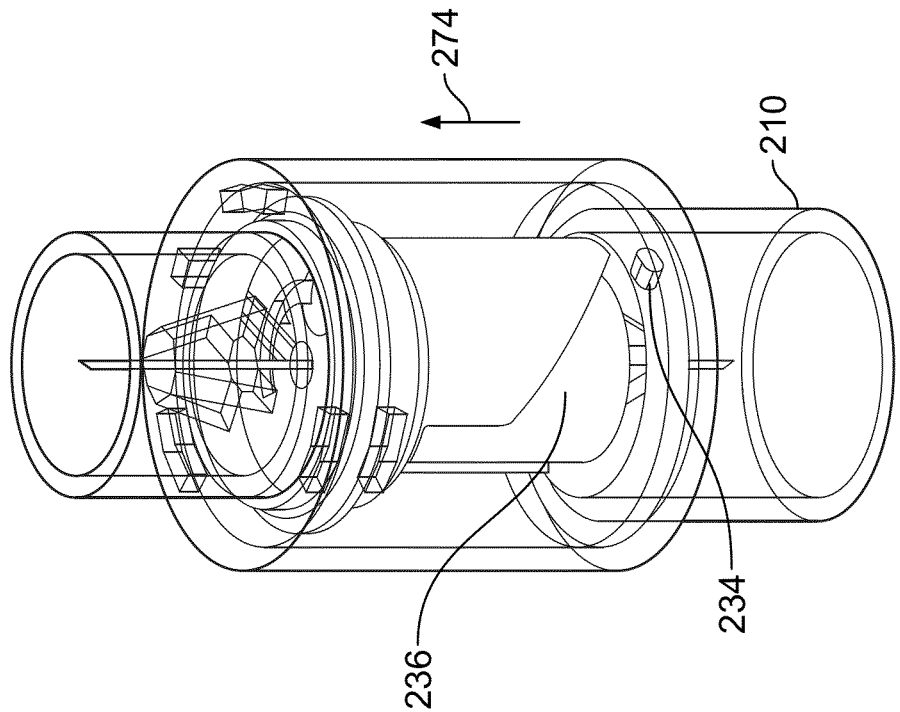
FIG. 16b
FIG. 16a

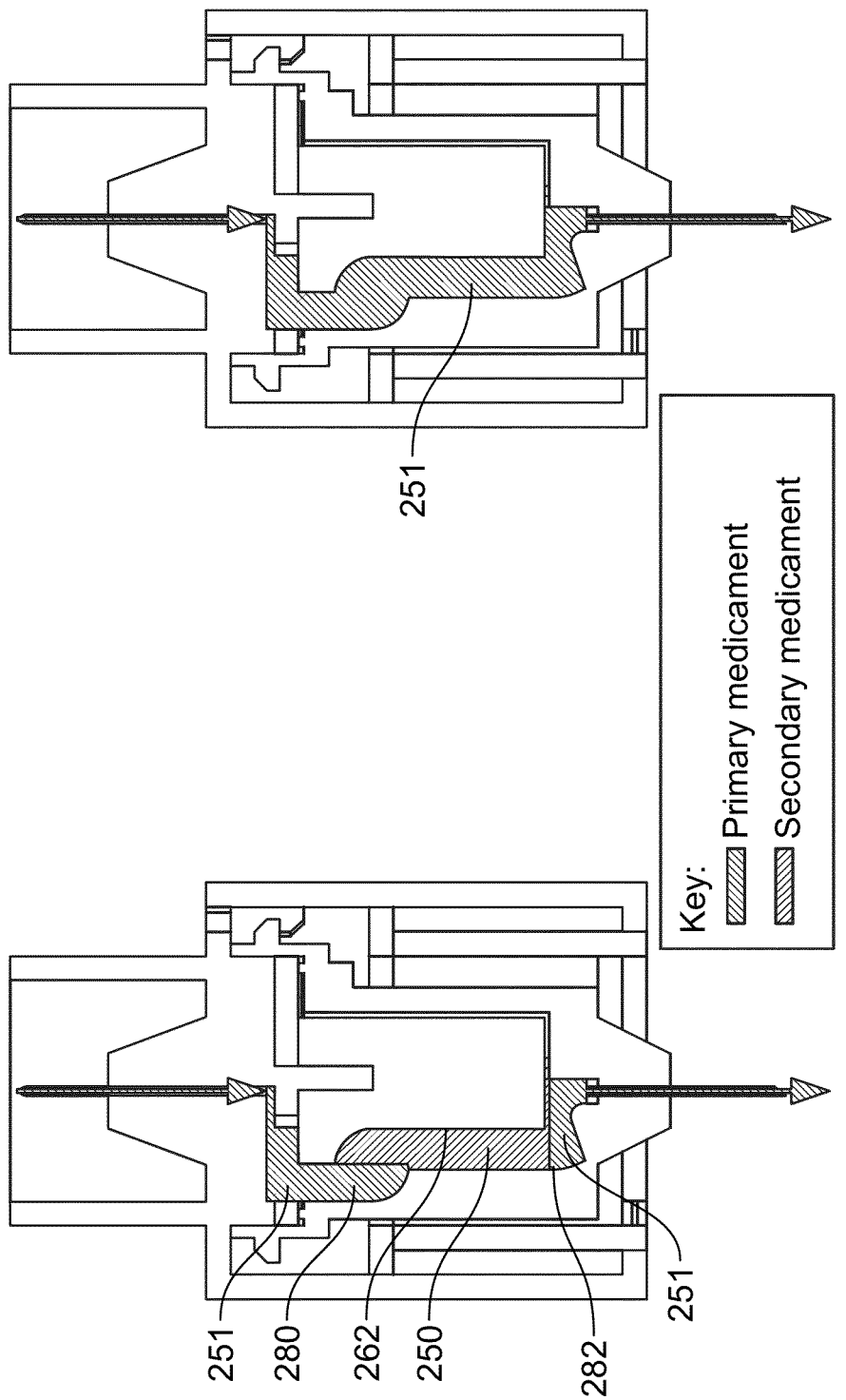

MEDICATED MODULE FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2012/057159 filed Apr. 19, 2012, which claims priority to European Patent Application No. 11163400.2 filed Apr. 21, 2011. The entire disclosure contents of these applications are herewith incorporated by reference into the present application.

FIELD OF INVENTION

This present patent application relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, this application concerns a medicated module that may be used with a drug delivery device.

BACKGROUND

Certain disease states require treatment using one or more different medicaments. Some drug compounds need to be delivered in a specific relationship with each other in order to deliver the optimum therapeutic dose. Applicants' proposed concept is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments.

Accordingly, there exists a strong need to provide devices and methods for the delivery of two or more medicaments in a single injection or delivery step that is simple for the user to perform. Applicants' proposed concept overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Applicants' proposed concept also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

Additionally, in some cases, accurate filling of a medicament reservoir for a medicated module may be difficult. For instance, accurate filling of the medicament and the incorporation of an amount of additional 'head-space' in the cavity in order to accommodate manufacturing and assembly tolerances may increase manufacturing costs. Further, it may be difficult to prevent air from entering the medicament cavity of the medicated-module reservoir. There is therefore also a need for a medicated module reservoir configured to prevent air from entering the medicament cavity of the medicated-module reservoir.

These and other advantages will become evident from the following more detailed description of the invention.

SUMMARY

The presently proposed devices and methods allow for complex combinations of multiple drug compounds within a single drug delivery system. Further, the presently proposed devices and methods allow the user to set and dispense at least two medicaments through one single dose setting mechanism and a single dispense interface. This single dose setter controls the dose setting mechanism of the device such that a predefined combination of the individual medicaments is delivered when a single dose of one of the medicaments is set and dispensed through the single dispense interface.

By defining the therapeutic relationship between the individual medicaments, the proposed delivery device and delivery methods help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases or powders that are capable of flowing and that change shape at a steady rate when acted upon by a force tending to change its shape. Alternatively, one or both of the medicaments may be a solid that is carried, solubilized or otherwise dispensed with another fluid medicament.

Applicants' proposed concept is of particular benefit to users with dexterity or computational difficulties as the single input and associated predefined therapeutic profile removes the need for them to calculate their prescribed dose every time they use the device and the single input allows considerably easier setting and dispensing of the combined compounds.

In an example, a master drug compound, such as insulin, contained within a multiple dose, user selectable drug delivery device could be used with a single use, user replaceable, medicated module that contains a single dose of a secondary medicament and the single dispense interface. When connected to the primary drug delivery device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed method and system.

For the purposes of Applicants' proposed method and system the term "insulin" shall mean Insulin, insulin analogs, insulin derivatives or mixtures thereof, including human insulin or a human insulin analogs or derivatives. Examples of insulin analogs are, without limitation, Gly (A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In accordance with an embodiment of Applicants' disclosure, a medicated module is configured to minimize or eliminate the presence of air in the primary medicament cavity in a reservoir of the medicated module. Similarly, a method for filling a medicated module reservoir assembly that minimizes or eliminates the presence of air in the primary medicament cavity in the reservoir of the medicated module is provided.

According to an example, a medicated module is attachable to a drug delivery device that holds a first medicament. The medicated module comprises a rotatable reservoir body comprising (i) a flow path and (ii) a medicament-reservoir profile. The medicated module further comprises a pin feature disposed in the rotatable reservoir body, where the pin feature includes a medicament-cavity profile. The medicated module also includes a second medicament, wherein the second medicament is held in a reservoir region formed at least in part by the medicament-reservoir profile and the medicament-cavity profile. In addition, prior to dispense, the second medicament is filled to at least a proximal end of the medicament-cavity profile.

A particular benefit of Applicants' method and system is that the potential for air to be contained in the medicament that is ultimately dispensed from the medicated module is reduced or minimized. In an example, only a subset volume of the medicament volume filled into the medicated module is actually dispensed, and this subset volume is substantially free of air due to the configuration of the medicated module reservoir region and the filling process.

A medicated module in accordance with Applicants' proposed concept can be designed for use with a delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

In an example, the primary drug delivery device is used more than once and therefore is a multi-use device; however, the drug delivery device may also be a single use disposable device. Such a device may or may not have a replaceable reservoir of the primary drug compound, but Applicants' proposed concept is equally applicable to both scenarios. It is also possible to have a suite of different medicated modules for various conditions that could be prescribed as one-off extra medication to patients already using a standard drug delivery device. Should the patient attempt to reuse a previously used medicated module, features may be present that prevent reattachment to a primary drug delivery device or that prevent or discourage subsequent dosing through the needle via alternative means. For example, this medicated module may include a locking needle guard that is activated after a user delivers a dose from the medicated module. Other means of alerting the user may include some (or all) of the following:

Physical prevention of medicated module re-attachment to the primary drug delivery device once the module has been used and removed.

Physical/hydraulic prevention of subsequent liquid flow through the drug dispense interface once it has been used.

Physical locking of the dose setter and/or dose button of the primary drug delivery device.

Visual warnings (e.g., change in color and/or warning text/indicia within an indication window on the module once insertion and/or fluid flow has occurred).

Tactile feedback (presence or absence of tactile features on the outer surface of the module hub following use).

A further beneficial feature is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates a perspective view of one possible drug delivery device that can be used with Applicants' proposed medicated module;

FIG. 2a illustrates a perspective view of an example medicated module;

FIG. 2b illustrates a perspective, cross-sectional view of the example medicated module of FIG. 2a;

FIG. 3 illustrates a perspective, cross-sectional view of an example outer body of the example medicated module of FIG. 2a;

FIG. 4 illustrates a perspective view of an example plate feature of the example medicated module of FIG. 2a;

FIG. 5 illustrates a perspective view of an example needle guard of the example medicated module of FIG. 2a;

FIG. 6a illustrates a perspective view of an example rotatable reservoir body of the example medicated module of FIG. 2a;

FIG. 6b illustrates a perspective, cross-sectional view of the example rotatable reservoir body of the example of FIG. 6a;

FIG. 7 illustrates a perspective view of an example pin feature of the example medicated module of FIG. 2a;

FIG. 8a illustrates the example pin feature of FIG. 7 being inserted into the example rotatable reservoir body of FIG. 6a;

FIG. 8b illustrates a perspective, cross-sectional view of the example pin feature of FIG. 7 being inserted into the example rotatable reservoir body of FIG. 6a;

FIG. 9 illustrates the example pin feature of FIG. 7 inserted in the example rotatable reservoir body of FIG. 6a;

FIG. 10a illustrates an example stage of a filling process for the medicated module of FIG. 2a;

FIG. 10b illustrates an cross-sectional view of an example stage of a filling process for the medicated module of FIG. 2a;

FIG. 11a illustrates an example stage of an assembly process for the medicated module of FIG. 2a;

FIG. 11b illustrates an example stage of the assembly process for the medicated module of FIG. 2a;

FIG. 12a illustrates an example stage of the assembly process for the medicated module of FIG. 2a;

FIG. 12b illustrates an example stage of the assembly process for the medicated module of FIG. 2a;

FIG. 13a illustrates an example stage of the assembly process for the medicated module of FIG. 2a;

FIG. 13b illustrates an example stage of the assembly process for the medicated module of FIG. 2a;

FIG. 14a illustrates a perspective view of an example bypass function for the medicated module of FIG. 2a;

FIG. 14b illustrates a cross-sectional view of the example bypass function for the medicated module of FIG. 2a;

FIGS. 15a-b illustrate an example switch from priming mode to injection mode for the medicated module of FIG. 2a;

FIGS. 16a-e illustrate another view of the example switch from priming mode to injection mode for the medicated module of FIG. 2a;

FIG. 17 illustrates a cross-sectional view of the medicated module of FIG. 2a after priming but prior to dispense; and FIG. 18 illustrates a cross-sectional view of the medicated module of FIG. 2a after dispense.

DETAILED DESCRIPTION

Figure 3:
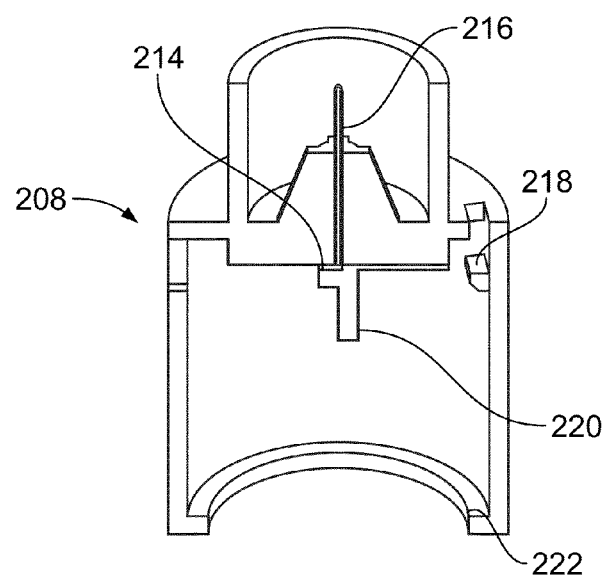

Applicants' proposed concept administers a fixed predetermined dose of a secondary medicament and a variable dose of a primary or first medicament through a single output or drug dispense interface. Setting and dispensing the dose of the primary medicament by the user automatically dispenses the fixed dose of the second medicament. The proposed concept relates specifically to a method and system that involves filling a medicated-module reservoir with a larger volume of the second medicament than is required for dispense, and for capturing a known subset volume from this medicated module in a manner that minimizes the potential for air to be contained in the second medicament that is ultimately dispensed from the medicated module.

A medicated module in accordance with embodiments of Applicants' proposed concepts may be attached to a primary drug delivery device. FIG. 1 illustrates one example of a drug delivery device 100 to which a medicated module, such as the medicated module 200 depicted in detail in FIGS. 2-18, can be attached. Specifically, the medicated module 200 can be attached to the connection means 109 of distal end 132. A medicated module in accordance with Applicants' proposed concept is preferably self-contained and provided as a sealed and sterile disposable module that has an attachment means compatible to the attachment means 109 at the distal end 132 of device 100. Although not shown, the medicated module could be supplied by a manufacturer contained in a protective and sterile container, where the user would peel or rip open a seal or the container itself to gain access to the sterile medicated module. Further, the drug delivery device 100 includes a housing including a single dose setter 112. The dose setter 112 may be operably connected to a primary reservoir of medicament that may be stored in the drug delivery device, such as in cartridge holder 115. The user may use a dose dial button 113 in order to dial a user selectable dose of the primary medicament.

In an example, proper filling of a reservoir of a medicated module may rely on accurate filling of the medicament and the incorporation of an amount of additional 'head-space' in the medicament cavity in order to accommodate manufacturing and assembly tolerances. Such a filling process may result in the presence of air in the medicament reservoir after filling and closure which—in extreme tolerance conditions, for example—may have the potential to detrimentally reduce the delivered dose volume from the medicated module. One possible solution would be to tighten the tolerances of both the reservoir geometry and the tolerances on the fill accuracy of the filling equipment. However, this solution route would likely increase manufacturing costs and/or manufacturing complexity, and thus is not ideal for high volume, rapid throughput manufacturing.

Thus, in accordance with Applicants' proposed concept, a medicated module is provided that address these concerns. As mentioned above, the medicated module in accordance with Applicants' disclosure beneficially results in little or no air being present in the medicament cavity that stores the medicament that is ultimately dispensed.

The proposed medicated module increases the nominal fill volume relative to the medicament cavity volume. Beneficially, this may reduce the challenges associated with filling the device due to the small volume (e.g., in the range of 20-60 microliters) required by the medicament cavity profile. In addition, the geometry of the medicated module reservoir region is such that, during the filling process, air is likely to accumulate in a known, controlled location (e.g., the top of the reservoir region). By capturing the excess air into a known, controlled location, it is then possible to design the medicated module to take out a known subset volume of this medicament from a region that is separate from this air-pocket, thereby reducing or minimizing the potential for air entrapment in the medicament cavity profile and thus minimizing its potential effect on the system dispense volume. In an example, it is similar to the way that an apple corer device removes the seeds from apples in a single action by removing material from the center of the apple, where the seeds are known to reside.

Applicants' proposed medicated module is attachable to a drug delivery device, such as drug delivery device 100, which includes a drug reservoir holding a first, primary medicament. The medicated module is designed and sized such that a known and substantial portion of the volume of the second medicament will be dispensed when the minimum required dose of the first medicament is dispensed from the primary device. In an example, the minimum required dose is 40 microliters or more; however, in other examples the minimum required dose may be less. So as to not waste medicament, which in some cases may be expensive, preferably at least 80% of the volume of the second medicament in the medicated module is dispensed when the minimum volume of the first medicament is dispensed from the primary drug delivery device 100.

In general, a medicated module in accordance with Applicants' proposed concept includes (i) a rotatable reservoir body comprising (a) a flow path and (b) a medicament-reservoir profile and (ii) a pin feature disposed in the rotatable reservoir body, the pin feature comprising a medicament-cavity profile. The medicated module also includes a second medicament that is held in a reservoir region formed at least in part by the medicament-reservoir profile and the medicament-cavity profile, and wherein, prior to dispense, the second medicament is filled at least to a proximal end of the medicament-cavity profile. The volume of medicament filled into the reservoir region is greater than the volume of the medicament-cavity profile.

FIGS. 2a-b illustrate an example medicated module 200 that may be used with a drug delivery device, such as drug delivery device 100. As shown in FIG. 2b, the medicated module 200 includes a rotatable reservoir body 202, a pin feature 204, a plate feature 206, an outer body 208, a needle guard 210, and a needle guard biasing member 212. The needle guard biasing member (e.g., a spring) may bias the needle guard in a distal direction so as to conceal the needle when the medicated module is not in use.

A cross-section of the outer body 208 is depicted in detail in FIG. 3. As shown, the outer body 208 includes a proximal flow channel 214 and a proximal needle 216. The proximal flow channel 214 allows medicament from the primary drug delivery device to flow through the proximal end of the outer body (and in particular to groove 232, which is described in detail below). In an example, the proximal needle could be bonded or insert molded into the outer body 208. The proximal needle 216 may establish fluid communication with the drug reservoir of the drug delivery device when the medicated module 200 is attached to the drug delivery device. Further, the outer body 208 includes a retaining feature, such as clip 218, configured to retain the rotatable reservoir body 202. The clip 218 may axially fix the rotatable body 202 to the outer body 208. Still further, the outer body 208 includes a keyed spigot 220 that is configured to (i) engage with the pin feature 204 and (ii) provide an axle for the plate feature 206. Yet still further, the outer body 208 may include a retaining feature, such as ridge 222, configured to engage with the needle guard 210.

Figure 4:
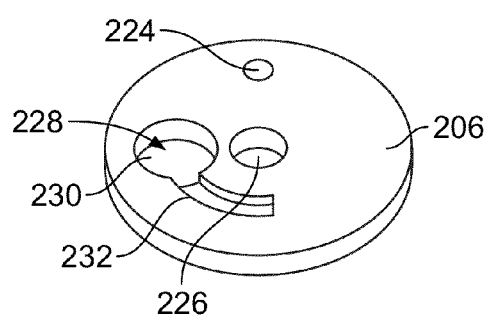

The plate feature 206 is depicted in detail in FIG. 4. As shown, the plate feature includes a hole 224, which may rotationally constrain the plate feature 206 to the rotatable reservoir body 202 by engaging with pip 247 (see FIG. 9). Further, the plate 206 may include another hole 226 that is configured to enable the plate to rotate relative to the keyed spigot 220 of the outer body 208. The plate feature 206 may also include a flow-section 228 that permits flow into the rotating reservoir body 202. In this example, the flow section 228 includes a hole 230 and a groove 232. The hole 230 permits flow into the rotating reservoir body 202, and the groove 232 may permit for medicament to flow from the proximal needle 216 to the hole 230.

Figure 5:
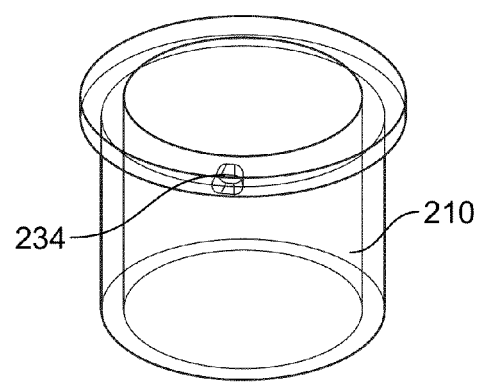

FIG. 5 depicts the needle guard 210, which may be similar to and operate in a similar fashion as certain needle guards known in the art. However, needle guard 210 may further include a tooth 234 that is designed to drive the helical cam surface 236 (see FIG. 6a) of the rotating reservoir body 202.

FIGS. 6a-b depict the rotatable reservoir body 202 in detail. The rotatable body 202 includes a ridge 238 near the proximal end 240 of the body, which may be used to engage with the clip 218 on the outer body 208. The rotatable body 202 further includes a helical cam surface 236, which is used to drive the rotation of the rotatable body 202. Further, a distal needle 242 may be attached to the rotatable body 202. In an example, the distal needle 242 could be bonded or insert molded into the rotatable body 202. This distal needle 242 may act as an outlet needle, through which the dose of the first and second medicament may be injected.

As shown in FIG. 6b, the rotatable reservoir body 202 may also include a flow path 244 that travels from the proximal end 240 to the distal end 246 of the rotatable body 202 (and in particular to the distal needle 242). In addition, the rotatable body includes a medicament-reservoir profile 248. The reservoir profile 248 may form a reservoir region for the medicament 250 (see FIG. 10b) when the pin feature 204 is inserted in the rotatable body 202. The flow path 244 and the medicament reservoir profile 248 may be cut-outs from the generally cylindrical interior of the reservoir body 202.

The rotatable reservoir body 202 may also include a seal or seals, such as complaint localized sealing beads 252. In an example, the localized sealing bead 252 may be twin-shot molded into the rotatable reservoir body 202. The sealing bead may be composed of, for example, thermoplastic elastomers (TPE) or silicon; however, other sealing materials are possible as well.

In addition, in an example, the main body of the rotatable body 202 is composed of a rigid inert polymer such as cyclo-olefin polymer (COP), high-density polyethylene (HDPE), or polypropylene (PP); however, other materials are possible as well.

The interior of the body 202 may be configured to receive pin 204. FIG. 7 depicts the pin feature 204 in detail. In this example, the pin feature 204 is a generally cylindrical pin feature, which allows the pin feature 204 to be disposed in the generally cylindrical interior of the rotatable reservoir body 202. The proximal end 256 of the pin feature 204 includes a keyed recess 258, and this recess 258 is configured to engage with the keyed spigot 220 on the outer body 208. The pin feature 204 also includes (i) a bypass flow path 260 and (ii) a medicament-cavity profile 262. The bypass flow path 260 and medicament-cavity profile 262 may be cut-outs from the generally cylindrical outer surface of the pine feature 204. The shapes of the illustrated cut-outs are intended as examples only; thus, cut-outs of other shapes (and sizes) are possible as well. When pin 204 is inserted into the rotatable body 202, the sealing beads 252 may seal and isolate the bypass flow path 260 from the medicament-cavity profile 262.

Beneficially, a medicated module comprising the parts illustrated in FIGS. 2-7 may be assembled and filled so that there is little or no air present in the medicament cavity of the medicated module from which the second medicament is ultimately dispensed. In particular, the medicated module in accordance with Applicants' proposed concept may isolate a known volume in the medicament cavity such that air trapped in the isolated volume is minimized, thereby minimizing dispense-accuracy variability caused by expulsion of air from the storage container. The assembly and filling process is described in detail below with respect to FIGS. 8-13.

During assembly, the medicament-cavity profile 262 in the pin 204 is rotationally aligned with the medicament-reservoir profile 248 (see FIGS. 8a-b) and is forced down axially into place in direction 264 (see FIG. 8a). The local sealing beads 252 provide contact pressure to isolate the bypass flow path 244 and the medicament-reservoir profile 248. The sealing beads 252 may provide fluid-tight engagement, while allowing the pin feature 204 and rotatable body 202 to move rotationally relative to one another.

After the pin 204 is placed into the body 202, the second medicament 250 may be filled into the medicated module 200. As seen in FIGS. 10a-b, medicament 250 may be dispensed into the reservoir region 245 formed at least in part by the medicament-reservoir profile 248 and the medicament-cavity profile 262. The shape of the reservoir region 245 may encourage air to be driven from the reservoir region 245 during filling. The reservoir region 245 is filled until the medicament level reaches a point above the proximal end of the medicament-cavity profile 262 of the pin feature 204. For example, as seen in FIG. 10b, the medicament level 266 is above the proximal end (i.e. top) 268 of medicament-cavity profile 262. Filling the medicament 250 above the top of the medicament cavity profile 262 helps to ensure that minimal or no air is present in the medicament that occupies the medicament cavity profile 262. Further, as seen in FIG. 10b, the seal 252 prevents the medicament 250 from leaking out of the reservoir region formed by the medicament-reservoir profile 248 and the medicament-cavity profile 262.

Figure 11A:
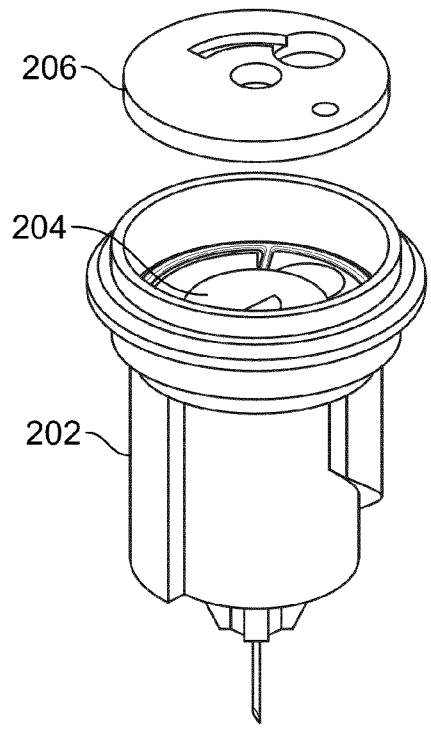
Figure 11B:
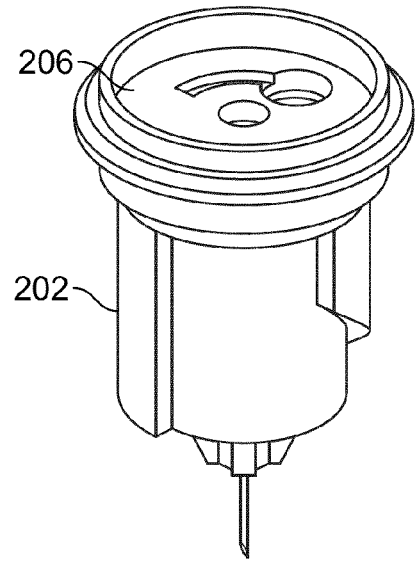

After the medicament 250 is filled into reservoir region 245, the plate 206 is rotationally aligned with the rotatable body 202 and lowered into place in direction 264, as seen in FIGS. 11a-b. Note that the plate feature 206 may be placed over the medicament-reservoir profile 248 and the medicament-cavity profile 262 to enclose the reservoir region 245 and seal the second medicament 250. The plate 206 may be secured in various ways. For instance, the diameter of the plate may substantially match the diameter of the rotatable body, such that it is difficult to remove the plate 206 from the rotatable body 202 once inserted. In another example, an adhesive may be applied to the distal end of the plate and/or the sealing beads 252. Further, as mentioned above, the proximal plate feature 206 may be keyed to the rotatable reservoir body 202 such that the proximal plate feature is rotationally fixed to the body 202.

Figure 12A:
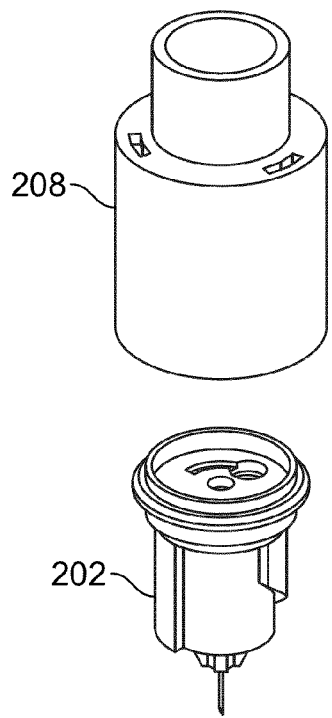
Figure 12B:
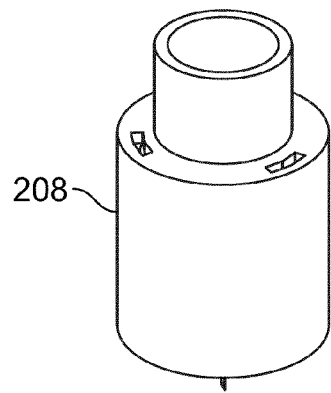
Figure 13B:
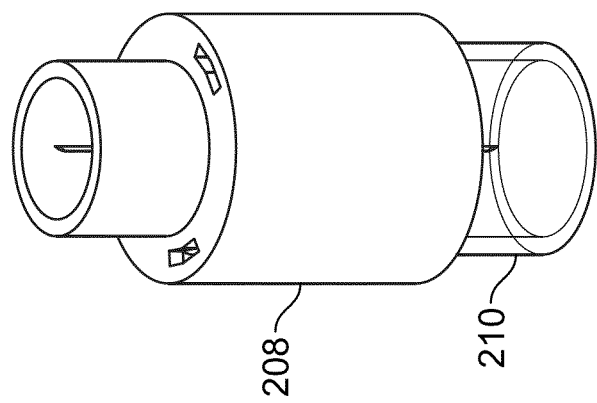
Figure 13A:
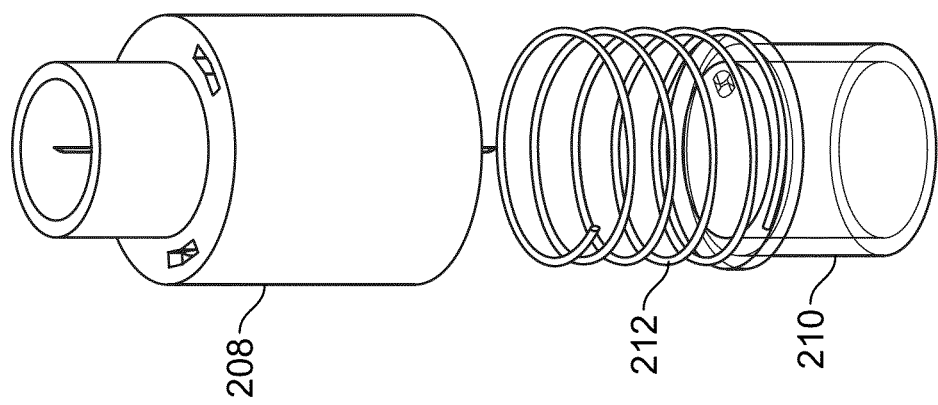

Next, the outer body 208 may then be attached (e.g., clipped) over the rotatable body 202, as seen in FIGS. 12a-b. The needle guard 210 and needle guard spring 212 may then be clipped into the outer body 208, as shown in FIGS. 13a-b. Note that although the example medicated module 200 includes the needle guard 210 as a way of driving the dose select system, alternatives such as a user input or a stored energy system are also possible.

After the module 200 is attached to the device 100, a user may set a user-settable dose of the first medicament 251. The dose of the first medicament 251 from the drug delivery device 100 may be set in a usual manner (e.g., by dialing out an appropriate number of units of the primary medicament 251 with a dose dial 113). Dispense of the second medicament 250 and the first medicament 251 may then be achieved via activation of the dosing mechanism of the drug delivery device 100. The operation of the medicated module 200 is described in detail below with respect to FIGS. 14-18.

Figure 14B:
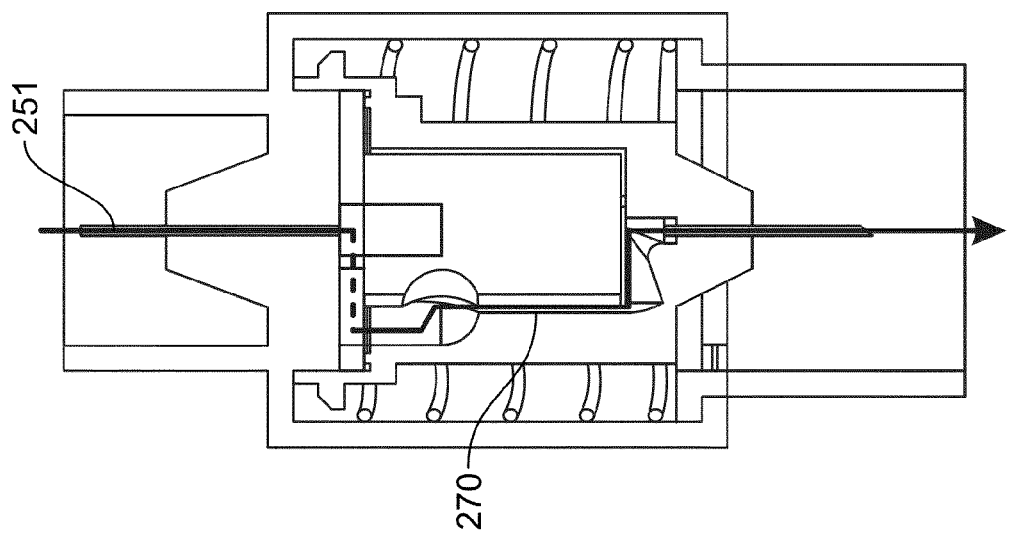
Figure 14A:
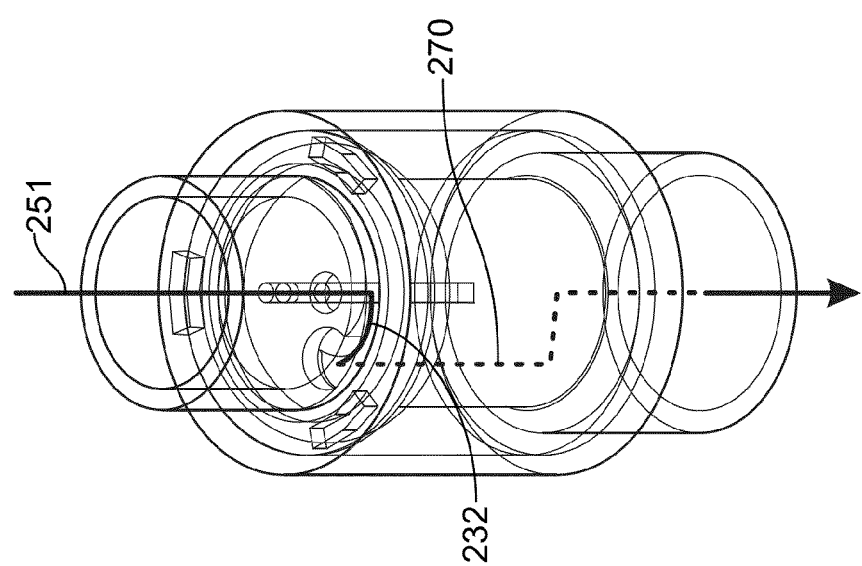

Prior to delivering a dose, a user may prime the drug delivery device 100. In particular, the user may prime the drug delivery device 100 with the first medicament 251 by forcing a priming dose of the first medicament 250 through the bypass flow path. FIGS. 14a-b depict the flow of the medicament through the bypass flow path of the medicated module 200. In particular, the bypass flow of the first medicament 251 is shown by arrow 270. As shown, the flow path runs from the outer body 208 around the groove 232 in the plate 206 and then down between the pin feature 204 and the rotatable body 202 (i.e., the flow path formed by the bypass flow path 260 and flow path 244). The bypass path avoids contact with the second medicament 250 stored in the medicated module. Note that although the example medicated 200 includes a bypass function to facilitate priming capability, other medicated modules in accordance with Applicants' proposed concept may not include such a bypass function.

After priming of the drug delivery device 100, the medicated module 200 may be switched from priming mode to injection mode. This switch between modes is described in detail with reference to FIGS. 15a-b and 16a-e. Generally, rotation of the rotatable body 202 (i) isolates the second medicament 250 stored in the medicament cavity profile 262 from the rest of the second medicament 250 and then (ii) aligns the medicament-cavity profile 262 with the flow path 244, thus enabling dispense of the second medicament 250 that is isolated in the medicament cavity profile 262. Note that the volume of the second medicament 250 that is isolated is less than the total volume of the second medicament 250 filled into the medicated module (e.g., compare FIG. 10b and FIG. 17).

Figure 15B:
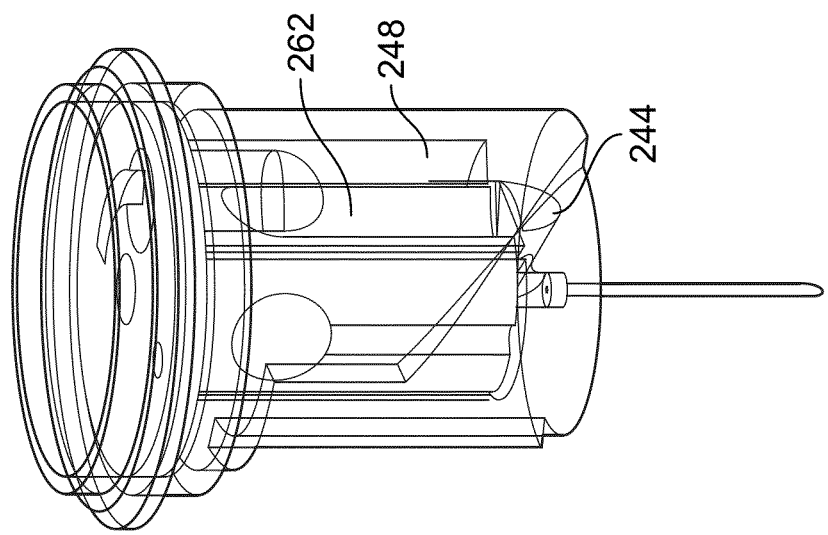
Figure 15A:
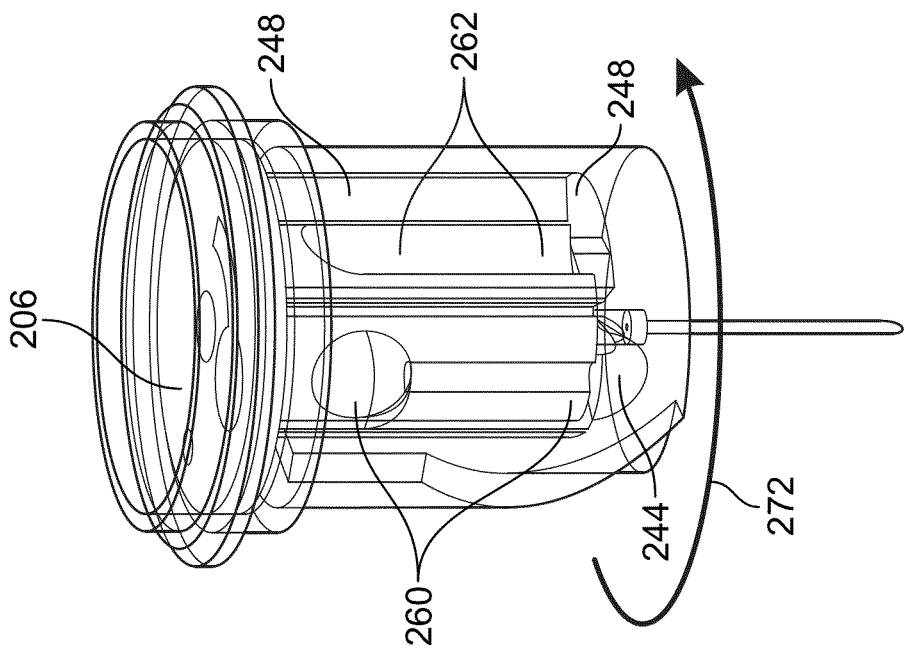

As seen in FIG. 15a, the bypass flow path 260 is initially rotationally aligned with the flow path 244. Further, the medicament-cavity profile 262 is initially aligned with the medicament-reservoir cavity 248. Rotation of the rotatable body 202 in rotational direction 272 rotates the rotatable body 202 relative to the pin feature 204. Further, since the plate 206 is rotationally fixed to the rotatable body 202, the plate 206 rotates with the rotatable body 202.

After the switch from bypass mode to injection mode, the bypass flow path 260 is sealed off and the medicament-cavity profile 262 is aligned with the flow path 244, as seen in FIG. 15b. Further, as mentioned above, the reservoir profile 248 is isolated from the medicament cavity profile 262. In particular, the rotation isolates the medicament 250 in the medicament cavity profile 262 from the other medicament 250 in the medicament reservoir profile 248. Therefore, the medicament 250 stored in the cavity is a controlled subset of the total medicament 250 filled into the medicated module 200. This controlled subset also has minimal to no air present in it because the medicament is filled to a level that is higher than the top of the medicament cavity profile 262.

As mentioned above, the needle guard 210 may force the rotation of the rotatable body 202. When a user presses the medicated module 200 against an injection site, the needle guard 210 moves in proximal direction 274. The helical cam surface 236 induces rotation of the rotatable body 202. In particular, the needle guard tooth 234 engages with the helical cam surface 236, and as the needle guard moves in proximal direction 274, the needle guard drives the rotation of the rotatable body 202. FIG. 16b shows the tooth 234 engaging with and traveling against the helical cam surface 236.

Figure 16C:
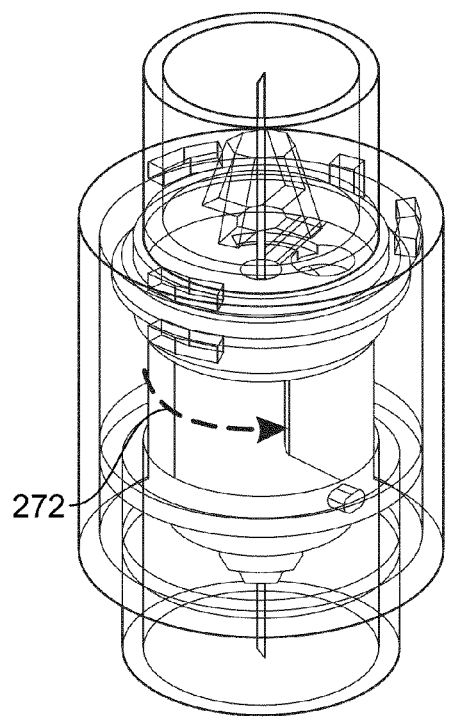

As seen in FIG. 16c, as the needle guard 210 is moved further in proximal direction 274, the rotatable body 202 rotates in direction 272. As mentioned above, the plate 206 is keyed to the rotatable body 202 and thus rotates along with the rotatable body 202; however, the pin 204 is keyed to the outer body 208 and thus does not rotate.

Figure 16D:
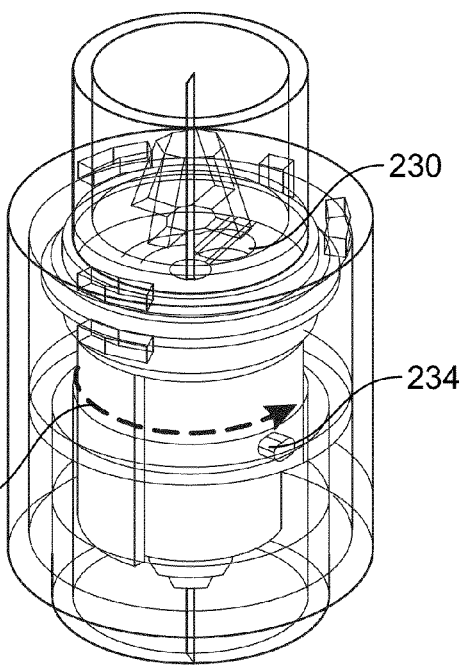
Figure 16E:
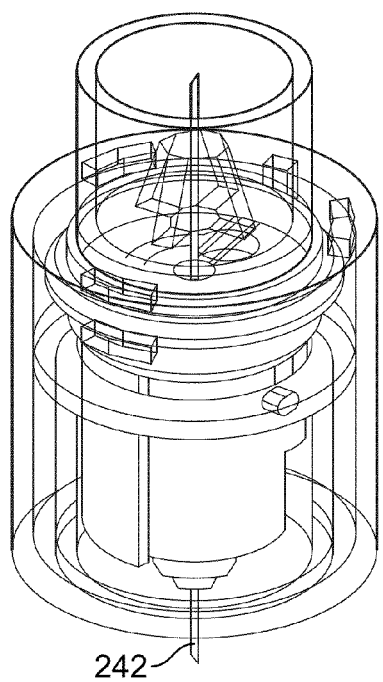

As seen in FIG. 16d, when the rotatable body 202 has reached its final rotational position, the tooth 234 disengages from the helical track 236. In this example, the needle guard 210 may travel further in proximal direction 274 to further expose the distal needle 242.

During the end of the rotation of the rotatable body 202, the hole 230 for permitting flow into the rotatable body 202 is located above the medicament cavity profile 262 (see FIG. 16b) rather than the bypass flow path 260 (see FIG. 15a). Thus, after the medicated module 202 switches from priming mode to injection mode, the medicaments 250, 251 may be dispensed through the medicated module 200. Dispense of both medicaments is shown in FIGS. 17-18.

FIG. 17 shows the medicated module 200 after priming is complete but prior to dispense. Residual prime fluid (i.e., medicament 251) collects in a region 280 above and a region 282 below the medicament-cavity profile 262. FIG. 18 shows the medicated module 200 during dispense, and in particular after the secondary medicament 250 stored in the medicament cavity 262 has been delivered. As seen, the entire flow path is filled with the primary medicament 251.

After the user finishes dispensing of the first medicament 251 and the second medicament 250, the user may remove the output needle 242 from the injection site. Then, the depleted medicated module 200 may be disconnected from the drug delivery device 100 and disposed of. Assuming that the drug delivery device 100 still holds some first medicament 251, the drug delivery device 100 may be reused by the patient as required.

As described above, Applicants' proposed concept beneficially allows for a medicated module that minimizes the potential for air to be contained in the medicament that is ultimately dispensed from the system (i.e., the medicament that is stored in medicament cavity 262). Thus, such a medicated module may administer a highly accurate dose of the second medicament. The highly accurate amount of medicament dispensed from the medicated module may be varied by altering the shape and/or size of the medicament-cavity profile and/or medicament reservoir profile.

The connection or attachment between the medicated module of the above descried embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The shape of the medicated module may generally be a cylindrical body or any other geometric shape suitable for defining a fluid reservoir or for containing discrete self-contained reservoir of the medicament in the medicated module and for attaching one or more needle cannula. Generally, the medicated module can be manufactured from glass or other drug contact suitable material. The integrated output needle can be any needle cannula suitable for subcutaneous or intramuscular injection. In an example, the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user.

The medicated module of Applicants' concept should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical drug delivery device contains a cartridge or other reservoir of medication. This cartridge is typically cylindrical in shape and is usually manufactured in glass. The cartridge is sealed at one end with a rubber bung and at the other end by a rubber septum. The drug delivery pen is designed to deliver multiple injections. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, the drug delivery device having a drug reservoir holding a first medicament, the medicated module comprising:
   an outer body that houses a rotatable reservoir body that is rotatable with respect to the outer body;
   a second medicament;
   a proximal needle at the outer body, wherein the proximal needle is configured to establish fluid communication with the drug reservoir of the drug delivery device when the medicated module is attached to the drug delivery device;
   a distal needle attached to the rotatable reservoir body, wherein the distal needle is configured to act as an output needle, through which a dose of the first medicament and the second medicament can be injected; and
   a pin feature disposed in the rotatable reservoir body, the pin feature comprising a medicament-cavity profile and a bypass flow path, wherein the pin feature is rotationally fixed to the outer body;
   wherein the rotatable reservoir body comprises (i) a flow path traveling from a proximal end to a distal end of the rotatable reservoir body, and (ii) a medicament-reservoir profile, wherein the rotatable reservoir body is axially fixed to the outer body;
   wherein the second medicament is held in a reservoir region formed at least in part by the medicament-reservoir profile and the medicament-cavity profile, and wherein, prior to dispense, the second medicament is filled to at least a proximal end of the medicament-cavity profile; and
   wherein the rotatable reservoir body is configured to rotate with respect to the pin feature from a priming mode to an injection mode such that (i) prior to dispense, (a) the bypass flow path is initially in communication with the flow path such that the drug delivery device may be primed with the first medicament by forcing a priming dose of the first medicament through the bypass flow path, and (b) the medicament-cavity profile is in communication with the reservoir profile, and such that and (ii) during dispense, the medicament-cavity profile is in communication with the flow path such that the first and the second medicament may be delivered through the distal needle.

2. The medicated module of claim 1, wherein the outer body comprises a keyed spigot, and wherein the pin feature comprises a corresponding keyed recess configured to engage with the keyed spigot.

3. The medicated module of claim 1, further comprising a proximal plate feature, wherein the proximal plate feature is rotationally fixed to the rotatable reservoir body, wherein the proximal plate feature is configured to seal the second medicament.

4. The medicated module of claim 3, wherein the proximal plate feature comprises at least one hole to permit flow into the rotatable reservoir body.

5. The medicated module of claim 4, wherein the proximal plate feature comprises a groove configured allow for the first medicament to flow from a proximal needle to the hole.

6. The medicated module of claim 2, wherein the proximal plate feature comprises a hole configured to permit the proximal plate feature to rotate relative to the keyed spigot of the outer body.

7. The medicated module of claim 6, wherein the proximal plate feature is keyed to the rotatable reservoir body such that the proximal plate feature is rotationally fixed.

8. The medicated module of claim 1, further comprising a needle guard, wherein the needle guard is configured to rotate the rotatable reservoir body as the needle guard is moved in a proximal direction.

9. The medicated module of claim 8, wherein the needle guard comprises a tooth feature, wherein the rotatable reservoir body comprises helical cam surface configured to interact with the tooth feature as the needle guard rotates the rotatable reservoir body.

10. The medicated module of claim 1, wherein the second medicament dispensed from the medicated module is medicament stored in the medicament cavity profile.

11. The medicated module of claim 1, wherein rotation of the rotatable body causes the second medicament stored in the medicament cavity profile to be isolated from the rest of the second medicament, wherein the volume of the second medicament that is isolated is less than the total volume of the medicament filled into the medicated module.

12. The medicated module of claim 1, wherein the medicament-reservoir profile and the flow path are cut-outs from the generally cylindrical interior of the reservoir body and
   wherein the medicament-cavity profile and the bypass flow path are formed by cut-outs from the generally cylindrical outer surface of the pin feature;
   wherein
   (i) prior to dispense, (a) the bypass flow path is initially rotationally aligned with the flow path such that the drug delivery device may be primed with the first medicament by forcing a priming dose of the first medicament through the bypass flow path and (b) the medicament-cavity profile is rotationally aligned with the reservoir profile,
   wherein
   (ii) during dispense, the medicament-cavity is rotationally alighted with the flow path.

* * * * *